US010888238B2

(12) United States Patent
Allavatam et al.

(10) Patent No.: US 10,888,238 B2
(45) Date of Patent: *Jan. 12, 2021

(54) AUTOMATIC DETERMINATION AND SELECTION OF FILTERING IN A CARDIAC RHYTHM MANAGEMENT DEVICE

(71) Applicant: CARDIAC PACEMAKERS, INC., St. Paul, MN (US)

(72) Inventors: Venugopal Allavatam, Saratoga, CA (US); Stephen J. Hahn, Shoreview, MN (US); Keith L. Herrmann, Minneapolis, MN (US); Mitchell D. Lanz, Maple Grove, MN (US); Krzysztof Z. Siejko, Maple Grove, MN (US); Benjamin Speakman, Eagan, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 117 days.

This patent is subject to a terminal disclaimer.

(21) Appl. No.: 16/177,884

(22) Filed: Nov. 1, 2018

(65) Prior Publication Data

US 2019/0069793 A1 Mar. 7, 2019

Related U.S. Application Data

(63) Continuation of application No. 15/362,862, filed on Nov. 29, 2016, now Pat. No. 10,149,627.

(Continued)

(51) Int. Cl.
*A61B 5/0402* (2006.01)
*A61B 5/0452* (2006.01)
(Continued)

(52) U.S. Cl.
CPC ...... *A61B 5/04017* (2013.01); *A61B 5/04012* (2013.01); *A61B 5/0422* (2013.01);
(Continued)

(58) Field of Classification Search
None
See application file for complete search history.

(56) References Cited

U.S. PATENT DOCUMENTS 4,880,004 A   11/1989  Baker et al.
5,188,117 A    2/1993  Steinhaus et al.
(Continued)

OTHER PUBLICATIONS

Joseph D. Bronzino. The Biomedical Engineering Handbook. Third Edition. Medical Devices and Systems. Downloaded Jun. 15, 2018. 19 pages.

(Continued)

*Primary Examiner* — Brian T Gedeon
(74) *Attorney, Agent, or Firm* — Seager, Tufte & Wickhem LLP

(57) ABSTRACT

Methods and/or device facilitating and selecting among multiple modes of filtering a cardiac electrical signal, in which one filtering mode includes additional high pass filtering of low frequency signals, relative to the other filtering mode. The selection filtering modes may include comparing sensed signal amplitude to one or more thresholds, using the multiple modes of filtering. In another example, an additional high pass filter is enabled, over and above a default or baseline filtering mode, and the detected cardiac signal is monitored for indications of possible undersensing, and/or for drops in amplitude toward a threshold, and the additional high pass filter may be disabled upon finding of possible undersensing or drop in signal amplitude.

20 Claims, 8 Drawing Sheets

Related U.S. Application Data

(60) Provisional application No. 62/262,043, filed on Dec. 2, 2015.

(51) Int. Cl.
*A61N 1/39* (2006.01)
*A61N 1/37* (2006.01)
*A61N 1/362* (2006.01)
*A61B 5/00* (2006.01)
*A61B 5/0456* (2006.01)
*A61B 5/0428* (2006.01)
*A61B 5/042* (2006.01)
*A61B 5/04* (2006.01)

(52) U.S. Cl.
CPC .......... *A61B 5/0428* (2013.01); *A61B 5/0452* (2013.01); *A61B 5/0456* (2013.01); *A61B 5/04288* (2013.01); *A61B 5/725* (2013.01); *A61N 1/3627* (2013.01); *A61N 1/3702* (2013.01); *A61N 1/3925* (2013.01); *A61N 1/3956* (2013.01); *A61B 5/7282* (2013.01)

(56) References Cited

U.S. PATENT DOCUMENTS

| | | | |
|---|---|---|---|
| 5,255,186 A | 10/1993 | Steinhaus et al. | |
| 5,372,139 A | 12/1994 | Holls et al. | |
| 5,437,285 A | 8/1995 | Verrier et al. | |
| 5,709,215 A | 1/1998 | Perttu et al. | |
| 5,752,976 A | 5/1998 | Duffin et al. | |
| 5,871,507 A | 2/1999 | Obel et al. | |
| 6,438,409 B1 | 8/2002 | Malik et al. | |
| 6,754,528 B2 | 6/2004 | Bardy et al. | |
| 6,810,282 B2 | 10/2004 | Taha et al. | |
| 6,834,204 B2 | 12/2004 | Ostroff et al. | |
| 7,099,715 B2 | 8/2006 | Korzinov et al. | |
| 7,141,017 B2 | 11/2006 | Laske et al. | |
| 7,248,921 B2 | 7/2007 | Palreddy et al. | |
| 7,274,959 B1 | 9/2007 | Wang et al. | |
| 7,308,307 B1 | 12/2007 | Pei et al. | |
| 7,376,458 B2 | 5/2008 | Palreddy et al. | |
| 7,383,080 B1 | 6/2008 | Kil et al. | |
| 7,392,085 B2 | 6/2008 | Warren et al. | |
| 7,477,935 B2 | 1/2009 | Palreddy et al. | |
| 7,623,909 B2 | 11/2009 | Sanghera et al. | |
| 8,116,867 B2 * | 2/2012 | Ostroff | A61N 1/3621 600/515 |
| 8,160,686 B2 | 4/2012 | Allavatam et al. | |
| 8,160,687 B2 | 4/2012 | Warren et al. | |
| 8,200,341 B2 | 6/2012 | Sanghera et al. | |
| 8,565,878 B2 | 10/2013 | Allavatam et al. | |
| 8,666,489 B2 | 3/2014 | Ostroff | |
| 10,149,627 B2 | 12/2018 | Allavatam et al. | |
| 2004/0093037 A1 | 5/2004 | Henry | |
| 2004/0199082 A1 | 10/2004 | Ostroff et al. | |
| 2005/0182334 A1 | 8/2005 | Korzinov et al. | |
| 2007/0156056 A1 | 7/2007 | Min et al. | |
| 2010/0191132 A1 | 7/2010 | Jackson | |
| 2011/0178564 A1 | 7/2011 | Keefe | |
| 2012/0046563 A1 | 2/2012 | Allavatam et al. | |
| 2012/0123488 A1 | 5/2012 | Ostroff | |
| 2017/0112399 A1 | 4/2017 | Brisben et al. | |
| 2017/0113040 A1 | 4/2017 | Brisben et al. | |
| 2017/0113050 A1 | 4/2017 | Brisben et al. | |
| 2017/0113053 A1 | 4/2017 | Brisben et al. | |

OTHER PUBLICATIONS

International Search Report and Written Opinion dated Feb. 9, 2017 for International Application No. PCT/US2016/063914.

* cited by examiner

AUTOMATIC DETERMINATION AND SELECTION OF FILTERING IN A CARDIAC RHYTHM MANAGEMENT DEVICE

CROSS REFERENCE TO RELATED APPLICATIONS

The present application is a continuation of U.S. patent application Ser. No. 15/362,862, filed on Nov. 29, 2016, which claims the benefit of and priority to U.S. Provisional Patent Application Ser. No. 62/262,043, filed on Dec. 2, 2015, the disclosures of which are incorporated herein by reference.

BACKGROUND

A number of cardiac rhythm management products are available for the use in diagnosis and treatment of various conditions. These may include, for example, subcutaneous, transvenous, or intracardiac therapy devices such as pacemakers, defibrillators and resynchronization devices. Implantable, external and/or wearable cardiac monitors are also available. External or wearable therapy products may include defibrillator vests and external pacemakers, as well as automatic external defibrillators.

FIG. 1, which is taken from Ellenbogen, et al. in CLINICAL CARDAIC PACING AND DEFIBRILLATION, 2$^{nd}$ Ed. (W. B. Saunders Co. 2000), at 201, shows the frequency of raw cardiac signals and non-cardiac myopotentials. The signals include T-waves, which represent ventricular repolarization and have a frequency content in the range of about 3-9 Hz or so. R-waves are also indicated and represent ventricular depolarization; the R-wave frequency range is typically from about 20 Hz to about 40 Hz. P-waves, representing atrial depolarization, are still higher frequency, in the range of about 30-70 Hz. Myopotentials, representing non-cardiac muscle activity, tend to have frequency content of 90 Hz and above.

T-wave filtering may be desirable for systems subject to a risk of T-wave overdetection, which can lead to overcounting of cardiac cycles and possibly to inappropriate therapy. While filtering the T-wave out may reduce potential overdetection and inappropriate therapy, it is also necessary to ensure that filtering directed at the T-waves does not lead to undersensing of tachyarrhythmias such as ventricular fibrillation or polymorphic ventricular tachycardia. Such arrhythmias are often detected by monitoring for and counting the R-waves.

The concern arises because the signals for T and R waves are so close together in the frequency domain. For example, a first order high pass filter with a corner frequency at 10 Hz, which would attenuate the 3-9 Hz T-wave, will also attenuate a signal at 15 Hz by ten to twenty percent, or more, which can be significant. Given that barely a decade (a tenfold increase in frequency) separates the noted signals, the effect of a filter directed at one set of signals on other signals should be monitored.

New and alternative approaches to filtering control are desired.

OVERVIEW

The present inventors have recognized, among other things, that a problem to be solved is that of attenuating T-waves while monitoring detected signals in a cardiac rhythm management system to ensure that undersensing of R-waves and/or arrhythmias is avoided. To this end, one example provides a method or device facilitating and selecting among multiple modes of filtering, with one mode including additional high pass filtering of low frequency signals relative to the other filtering mode. In an example, over-attenuation of desirable cardiac signal such as the R-wave is avoided by comparing the detected signal amplitude to one or more thresholds, using multiple modes of filtering. In an example, an additional high pass filter is enabled, over and above a default or baseline filtering mode, and the detected cardiac signal is monitored for indications of possible undersensing, and/or for drops in amplitude toward a threshold, and the additional high pass filter may be disabled upon finding of possible undersensing or drop in signal amplitude.

This overview is intended to briefly introduce the subject matter of the present patent application, and is not intended to provide an exclusive or exhaustive explanation of the invention. The detailed description is included to provide further information.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
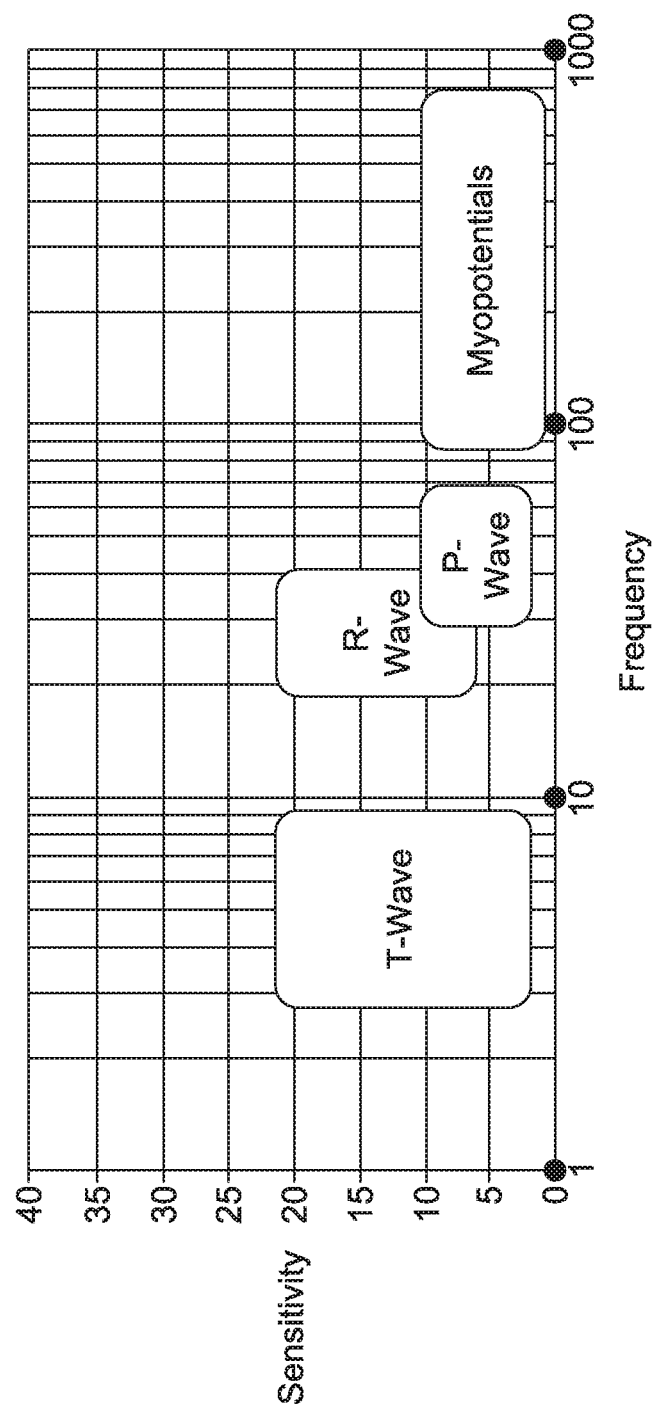
FIG. 1 shows the frequency content of certain biological signals.
Figure 2:
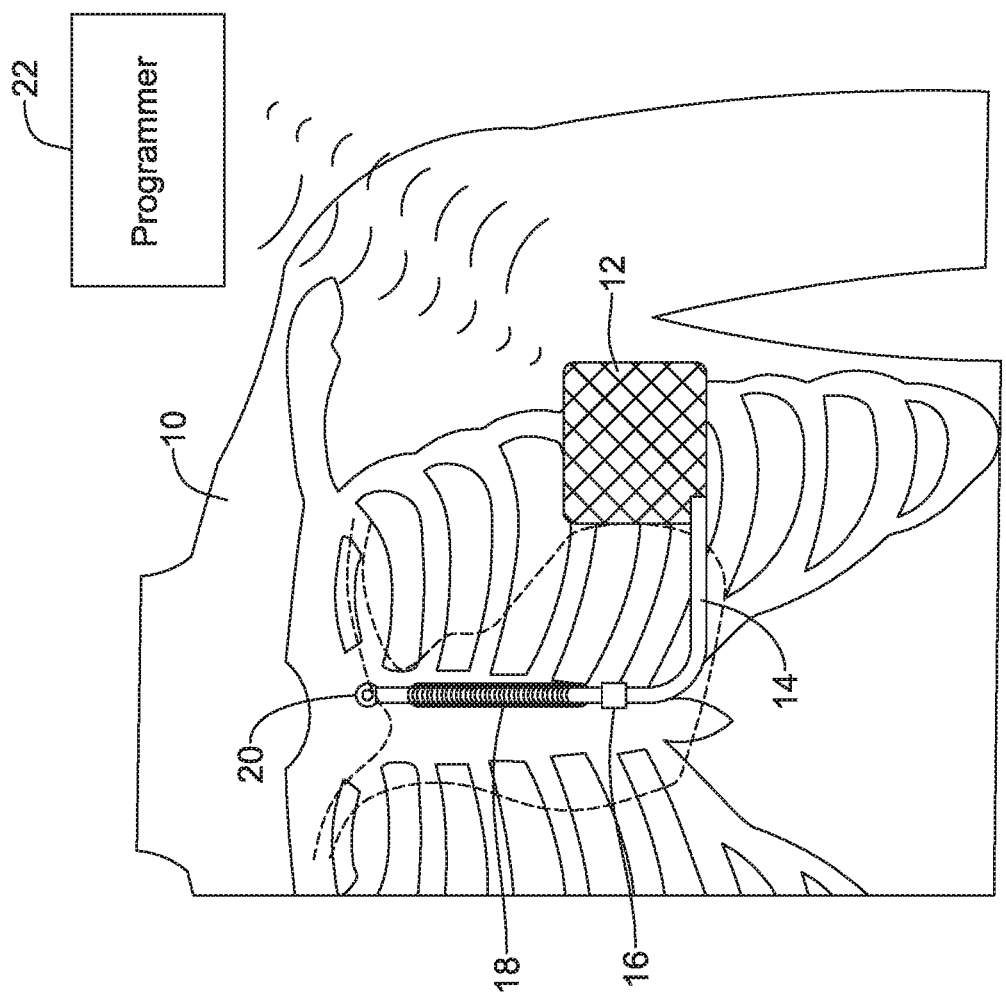
FIG. 2 shows an illustrative implantable medical device system.

FIG. 2 shows the S-ICD System™ from Cameron Health, Inc., and Boston Scientific Corporation, as implanted in a patient. The system is implanted in a patient 10 with a canister 12 in the left axilla at about the level of the cardiac apex. A lead 14 is placed subcutaneously, beneath the skin and over the ribcage of the patient, with a first portion extending along the inframammary crease to the xiphoid, and then superiorly parallel to and about 1-2 cm to the left of the sternum. A proximal sense electrode 16, shocking coil electrode 18, and distal tip sense electrode 20 are provided along the parasternal portion of the lead 14. The entire system is implanted outside of the ribcage.

The canister 12 may include componentry appropriate for communication (such as RF communication, inductive telemetry or other suitable communication linkage) with an external device such as a programmer 22. For example, during an implantation procedure, once the canister 12 and lead 14 are placed, the programmer 22 may be used to activate the canister 12 and/or direct/observe diagnostic or operational tests. After implantation, the programmer 22 may be used to non-invasively determine the status and history of the implanted device. The programmer 22 in combination with the canister 12 may also allow annunciation of statistics, errors, history and potential problems to the user/medical practitioner, and may also allow for updating of programming in the canister 12.

In some examples, the present invention may be implemented in a system as shown in FIG. 2. In other examples, an implantable or wearable cardiac monitor may have multiple electrodes on a housing and/or lead to define two or more sensing vectors. Leadless devices, such as leadless cardiac pacemakers for implantation inside the heart, may have multiple sensing electrodes on or extending from a canister or housing to define multiple sensing vectors. Wearable defibrillators or pacemakers may also provide multiple cutaneous electrodes on the anterior and/or posterior thorax of the patient, and may even include indifferent electrodes elsewhere such as on a limb. Transvenous and/or epicardial implantable devices may have an active housing adapted for use in sensing along with plural electrodes for sensing on one or more leads, as is well known in the art. For example, a transvenous device may have a right ventricular lead with atrial and ventricular sensing electrodes as well as an indifferent electrode on the canister. Alternative devices may also or instead use a lead beneath the ribs and outside of the heart such as in a substernal location.

Specific to the device shown in FIG. 2, unlike prior art defibrillators and pacemakers that included electrodes in or on the heart, the device uses only far-field electrodes outside the ribcage and away from the heart for detecting cardiac activity. This can make counting cardiac cycles more difficult, as the source of the detected signal may be harder to distinguish. For example, while a ventricular depolarization detected with a transvenous, intracardiac electrode may be quite sharp and narrow in width, the same signal will be wider and less sharp when detected in the far field. In some field products, T-wave overdetection has been observed in which individual cardiac cycles are counted twice, with a detection occurring on the R-wave and again on the T-wave. While significant effort is expended to avoid and/or identify and correct such overdetection, further improvements are desirable.

Figure 3:
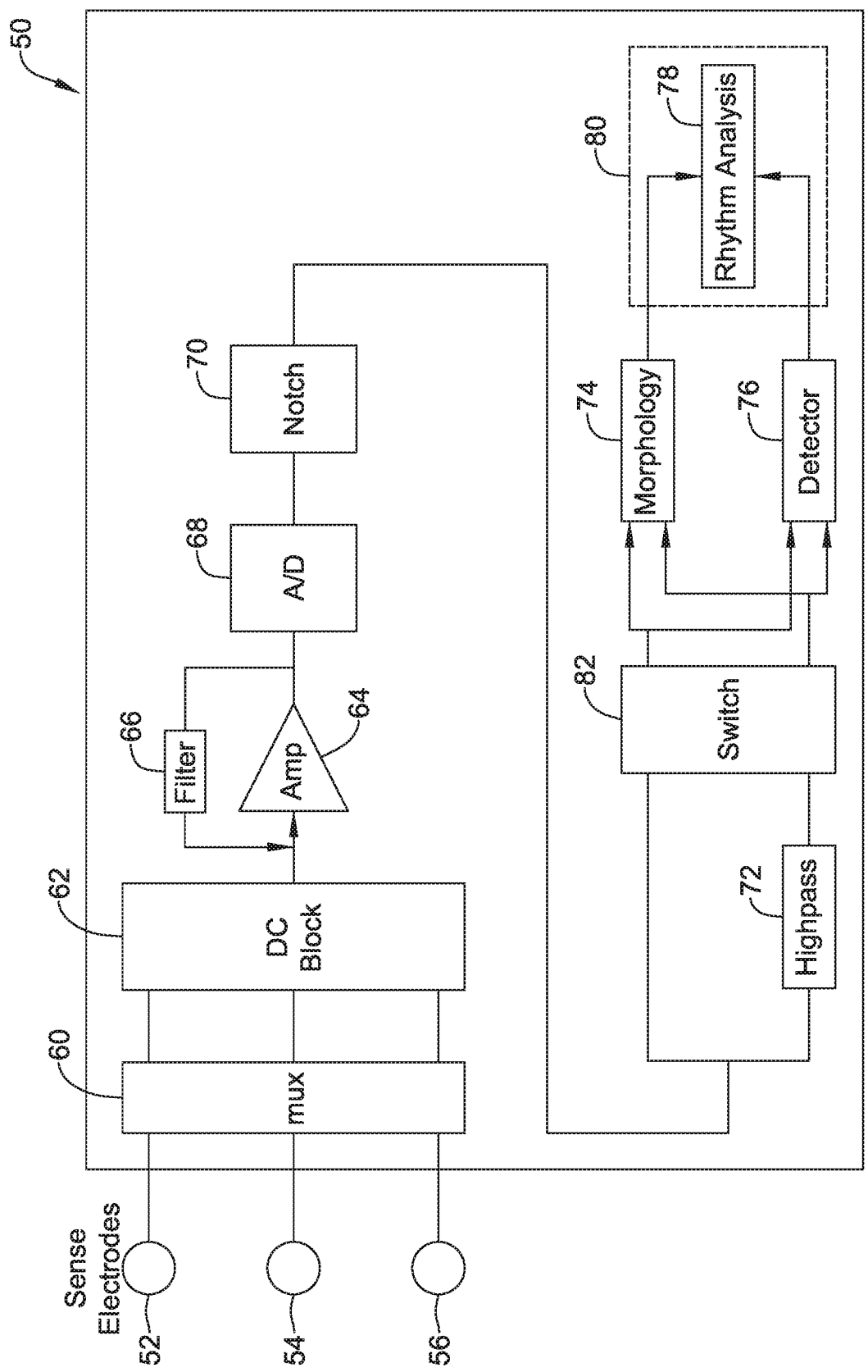
FIG. 3 provides a highly schematic depiction of an illustrative cardiac rhythm management device.

FIG. 3 provides a highly schematic depiction of an illustrative cardiac rhythm management device. The device 50 includes a plurality of electrodes 52, 54, 56, which may be provided on the housing of the device and/or in association with one or more leads. A multiplexor 60 may be provided to couple selected subsets of the electrodes 52/54/56 to the interior circuitry of the system. A set of DC blocking capacitors may be provided at 62 and the remaining signal passed onto an amplifier or plurality of amplifiers at 64. If desired elements 62 and 60 may be provided in opposite arrangement, or multiple DC blocking subcircuits 62 may be provided.

The amplifier stage 64 is associated with filter 66, which may be, for example, a low pass filter designed to block out higher frequency signals prior to reaching the analog-to-digital conversion (ADC) circuit 68. Any suitable ADC circuit 68 may be used, including a wide array of such devices known in the art including delta-sigma, successive approximation, Wilkinson, ramp-compare, delta encoded, pipeline, integrating, etc. The digital signal may then be notch filtered as indicated at 70 using, for example, a microprocessor or, in some embodiments, one or more digital signal processing chips.

At this point the signal can take two separate paths. In one path, the signal from the notch filter 70 goes directly to a morphology block 74, and is also fed to a cardiac cycle detector 76. The morphology block 74 is configured to store a set of data associated with a particular cardiac cycle and perform measurements and/or comparisons of the data including, for example, measurement of signal width and/or amplitude, slew rate, or other measurable features, as well as comparison to one or more static or dynamic templates using methods such as those in U.S. Pat. Nos. 7,477,935 and 7,376,458. The cardiac cycle detector 76 may be an R-wave detector or QRS complex detector using, for example, methods shown in U.S. Pat. Nos. 8,565,878 and/or 5,709,215, the disclosures of which are incorporated herein by reference. Though not shown, detected cardiac cycles may be certified by removing noise and/or overdetection using methods such as shown in U.S. Pat. Nos. 7,248,921, 8,160,686, and/or 8,160,687.

In the other path, the signal from the notch filter goes through a high pass filter stage 72 before going, again, to morphology block 74 and the cardiac cycle detector 76. The two "paths" may operate in parallel, or the device may be configured to engage the circuitry to use one path for a first period of time and the other path for a second period of time to allow later comparison.

The outputs of the cardiac cycle detector 76 and morphology block 74 are provided to a rhythm analysis block 78. The rhythm analysis block 78 may use various known methods for analyzing a patient's cardiac rhythm using, for example, a rate as calculated using the outputs of the cardiac cycle detector 76, as well as various shape features generated using the morphology block 74. Combinations of rate, width, amplitude, and matching to a template can be used to determine what is going on in the patient's heart. There may additionally be feedback paths to manipulate the operation of, for example, the multiplexor 60, notch 70, switch 82, and each of the morphology block 74 and cardiac cycle detector 76.

In some examples, as indicated, block 78 is performed by a controller 80 which may wake up in response to the output of the cardiac cycle detector 76. The controller 80 may be a microcontroller or microprocessor, for example, with associated memory for storing in a non-transitory medium instruction sets for performing various analyses. In other examples, different architectures may be used, for example, block 68 may be an ADC that is part of the controller 80, with each of blocks 70, 72, 74, 76 and 78 being performed by operable blocks of code stored in memory and accessed by the controller 80.

A switch is provided at 82 to allow selection between the signal coming out of the notch filter 70 or the signal from the additional highpass filter stage 72 for use in each of the morphology block 74 and the cardiac cycle detector. In some examples, if the highpass filter block 72 is not in use, it may also be powered down. In some examples, a combination of the notch 70 and highpass filter stage 72 operates as a first filtering configuration, and the notch 70 without the highpass filter stage 72 operates as a second filtering configuration, in which the first filtering configuration includes additional filtering relative to the second filtering configuration.

Figure 4:
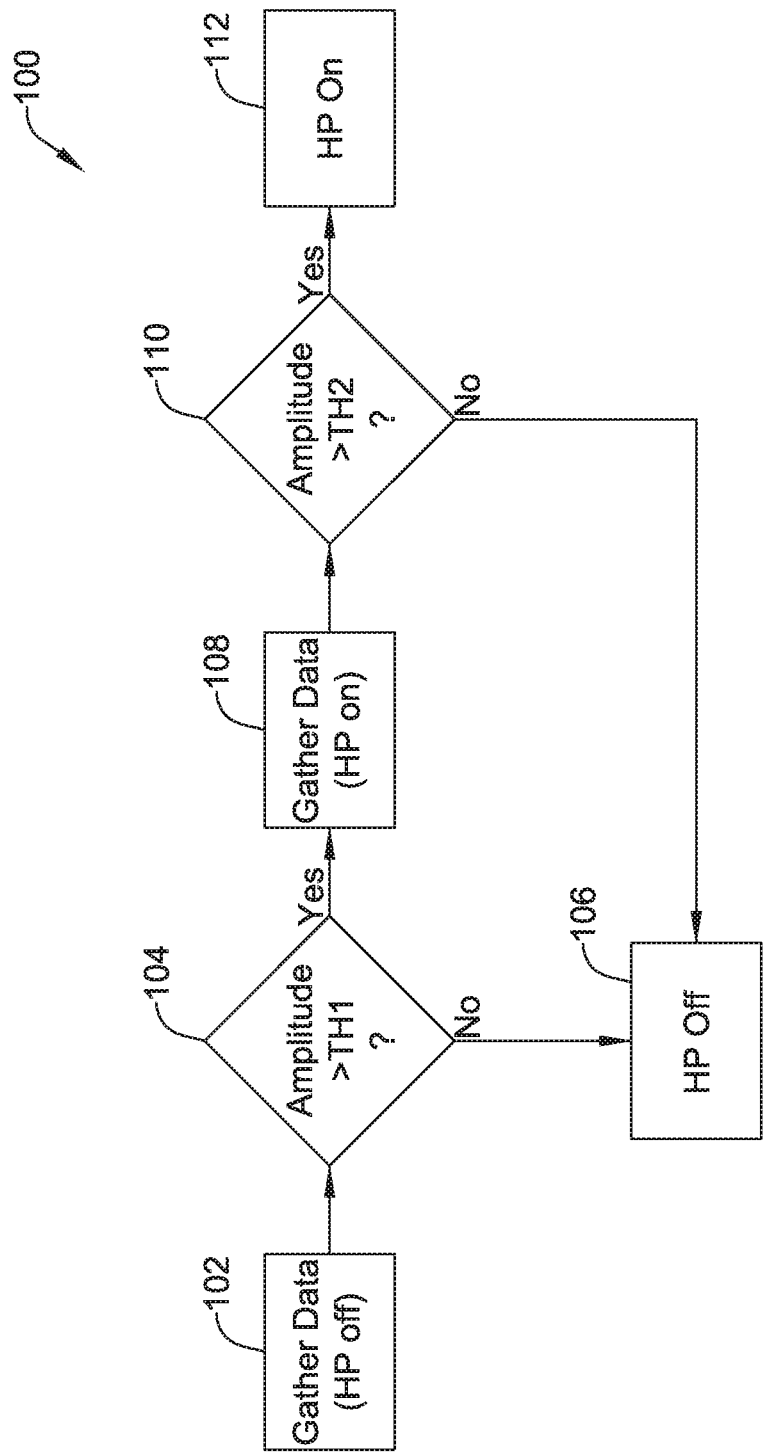
FIGS. 4-7 illustrate various methods in block flow form.

FIG. 4 shows an illustrative method in block flow form. This example 100 begins with gathering data in a cardiac rhythm management device in which at least one high pass ("HP") filter is off, as indicated (in short hand) at 102.

As used in one example, a standard or baseline filtering approach is taken with a pass band in the range of about 3 Hz to about 40 Hz, with additional notch filtering for line signals at 50 or 60 Hz. In this example, the HP filter is a high pass filter with a corner frequency at 9 Hz that is not on in the default approach, but which is available to be turned on if desired in addition to the default filtering. With the additional HP filter on, the passband would then be in the range of about 9 Hz to about 40 Hz, with additional filters again at the line frequencies (50 or 60 Hz), and another filter at 3 Hz that sits outside of the pass band.

These specific corner points for each filter may be varied in other examples. For example, a 4 Hz to 25 Hz passband may serve as default, with an extra 8 Hz filter applied optionally in one example. In another example, a 2 Hz to 50 Hz passband may be used by default with an additional high pass filter at about 7 Hz. These boundaries and passbands are noted here for cardiac signal purposes in particular. Those skilled in the art will recognize that other passbands and additional filter locations may be useful in other contexts, for example, when monitoring muscular or neurological activity in different parts of the body such as the diaphragm, digestive tract, spinal column, skeletal muscles, Vagus nerve, or brain.

A measure of amplitude of the gathered data is compared to a first threshold at 104. The measure of amplitude may take several forms. In some examples, cardiac cycle detection is performed to identify maximum peaks associated with cardiac cycles in the gathered data, and the maximum peaks are measured and/or averaged for comparison to the first threshold. In other examples, an average signal strength, such as a root-mean-square (RMS) amplitude is determined for the gathered data.

In one example, the first threshold is equal to about six times the noise floor of a given system. Other ratios may be used. In one illustrative embodiment, the first threshold is set to about 500 microvolts, for a system having an 80 microvolt noise floor. The comparison at 104 is intended ensure that the existing cardiac signal amplitude is well above the noise floor, since a high pass filter as envisioned in this example may well attenuate the cardiac signal. Therefore, if the amplitude measure is not greater than the threshold at 104, the high pass filter is left off, as indicated at 106.

If the test at 104 is passed, additional data is gathered, this time with the HP filter on as indicated at 108. Another comparison of an amplitude measure to a threshold is performed, as indicated at block 110. In one example, the amplitude measure at 110 is again a measure of the R-wave, while the threshold, TH2 is now a lower threshold, such as three times the noise floor, rather than six times the noise floor as previously discussed. As noted, other ratios may be used instead. If the second test at 110 is passed, then the HP filter is enabled or turned/left on 112. Otherwise, the HP filter is turned off or disabled, at 106. Returning to the example where the first threshold was 500 microvolts in a system having an 80 microvolt noise floor, in an example, the comparison at 110 uses the second threshold set to 250 microvolts, or about three times the noise floor. Other boundaries may be used.

Figure 5:
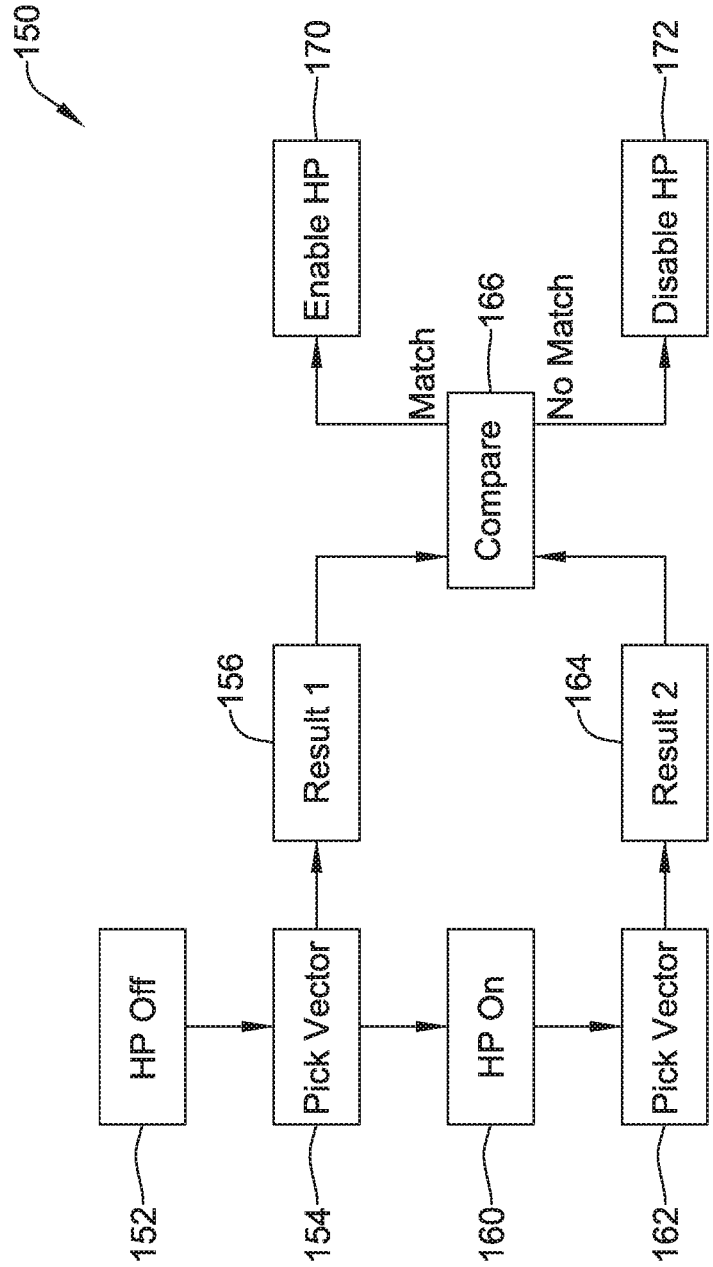

FIG. 5 shows an illustrative method in block blow form. The method 150 begins with the HP filter off, as indicated at 152. In this example, at least two sensing vectors are made available for use by the device; here, the next step is to perform vector selection, as indicated at 154. Vector selection may include operating a cardiac cycle detection method to identify a plurality of cardiac cycles and generate measurements of R-wave amplitude and/or signal to noise ratio, which may be assessed independently or combined together using various scoring methods. Any suitable vector selection method may be performed; some examples are in U.S. Pat. Nos. 7,392,085, 7,623,909, and 8,200,341, the disclosures of which are incorporated herein by reference. Vector selection may be reassessed if sensing signal quality drops or if other conditions are met, such as explained in U.S. Provisional Patent Application 62/245,757, and multiple vectors may be combined as explained in U.S. Provisional Patent Applications 62/245,738, 62/245,762, and 62/245,729, the disclosures of which are incorporated herein by reference. Whichever vector(s) is (are) selected is stored as Result 1, at 156.

Next, the HP filter is turned on, at 160, and vector selection is again performed as indicated at 162, this time using signals as filtered by the HP filter. The outcome of the second vector selection 162 is stored as result 2, at 164. These results are then compared at 166. If there is a match, that is, if the same sensing vector is chosen by both operations, then the HP filter is enabled, as indicated at 170. If Result 1 and Result 2 do not match, then the HP filter is disabled as indicated at 172.

In an example, the vector selection performed at block 154 may rely on each of signal to noise ratio and the amplitude of cardiac signals (e.g., as shown in U.S. Pat. No. 7,623,909). However, in some examples, since the HP filter is added in before vector selection at 162, only amplitude needs to be assessed. In other examples, the vector selection performed in each of blocks 154 and 162 is the same. In another example, if the signal to noise ratio is calculated at 154 and a very high signal to noise ratio is found, the inclusion of an HP filter may be unnecessary and so blocks 160/162 could be bypassed in response.

There are several variants on the method of FIG. 5. In one variation, a parallel processing method is performed in which vectors are selected with the HP filter on and off, and sensing/detection of cardiac cycles are performed on each of the two signals in parallel. The resulting cardiac signal detections are stored one-by-one, in temporally aligned fashion, at blocs 156 and 164. If the two sets of signal detections match—that is, if they are generally equal in number and occur at similar points in time, this indicates that the signal as detected with the HP filter on is detected much the same as that with the HP filter off, allowing for the HP filter to be enabled at 170. If there is a mismatch, this may be construed, in one example, as indicating that having the HP filter on is creating difficulties and therefore the HP filter is disabled at 172. In an alternative example, physician assessment may be requested to determine which of the HP filtered and not-filtered version of the signal is generated correct cardiac signal detection if there is a mismatch.

In an example, with reference to FIG. 5, result 1 at 156 may be a ratio of the average R-wave amplitude to the RMS signal for the vector picked at 154 while the HP filter is off. Continuing this example, result 2 at 156 may be a ratio of the average R-wave amplitude to the RMS signal for the vector picked at 162 while the HP filter is on. Whichever ratio is larger will determine whether the HP filter is enabled 170. For example, if the ratio is larger with the HP filter on, then the HP filter would be enabled. When such a comparison is made, the boundary conditions noted with respect to FIG. 4 may be used as well, to ensure that the average R-wave amplitude with the HP filter on is well above the noise floor.

Figure 6:
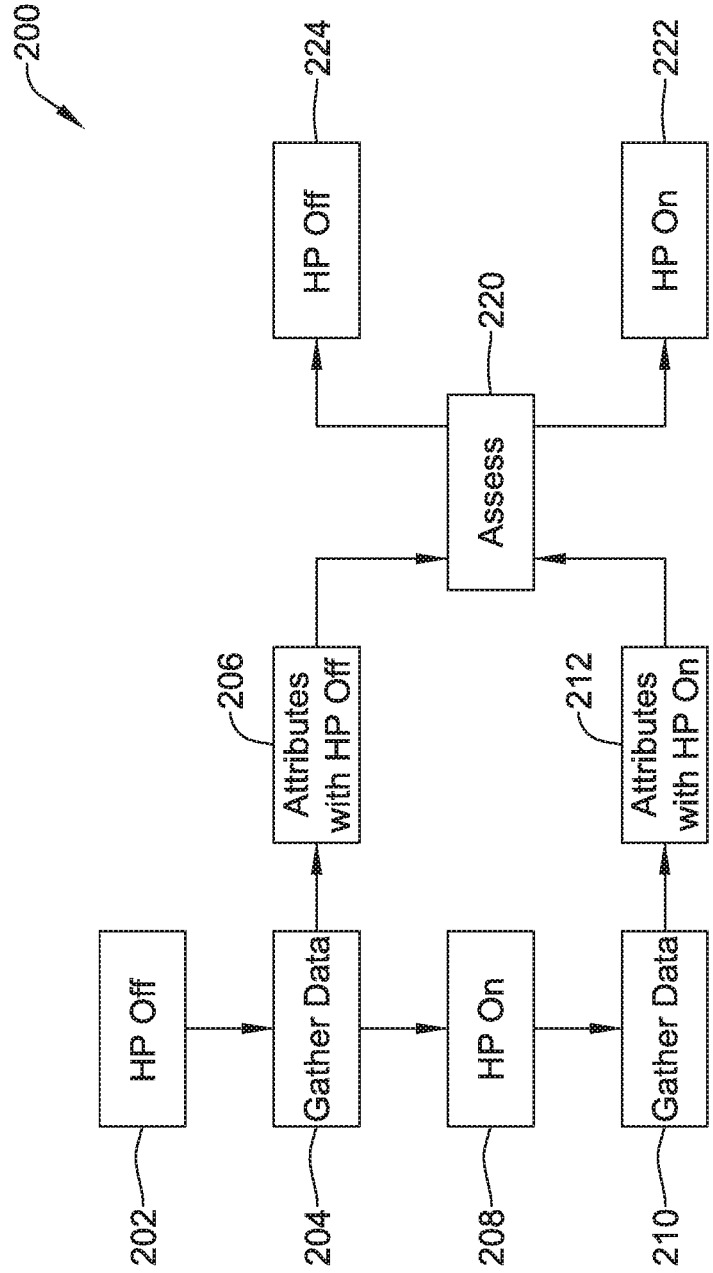

FIG. 6 shows an illustrative method in block flow form. The method 200 begins with the HP filter off, as indicated at 202. Data is gathered, for example by performing vector selection, or simply getting data on all vectors, and attributes of the signal as sensed with the HP filter off are generated and stored, as indicated at 206. The HP filter is then turned on at 208, and data is again gathered at 210 and attributes with the HP filter on are generated, as indicated at 212. An assessment is then made, at 220, as to how each of the sets of attributes suggest the system would perform with the HP filter off or on. The HP filter is then either turned on, at 222, or turned off, at 224.

In one example, the assessment at 220 may be constructed to prefer having the HP filter off. For example, the assessment at 220 may simply be whether the signal attributes at 212 are suitable for use; if so, then HP on is set at 222. If not, the assessment at 220 may simply turn the HP filter off, 224, or may also consider whether the attributes of the signal at 206 are adequate for use and, if not, an error flag or annunciator may be set to indicate that the system may not be functional.

In another example, the assessment at 220 may compare a signal to noise ratio calculated at 206 with a signal to noise ratio calculated at 212. If the signal to noise ratio at 212 is better, and if the amplitude of the signal at 212 is adequate, then the HP filter is set to on, at 222. Otherwise, the HP filter is set to off at 224.

In another example, the data gathered at 204 and 210 may include data generated over time by analyzing, for example, in a parallel processing scheme, cardiac signals captured with and without the HP filter on for a period of time that includes a number of cardiac cycles. The individually detected cardiac cycles may be analyzed to determine which of attributes 206 or attributes 212 suggests a likelihood of accurate detection. Some indicators may be, for example:

Signal to noise ratio and/or amplitude may serve in several examples, though more sophisticated approaches follow. To the extent signal to noise ratio is a factor, it may be calculated in any suitable manner such as, for example and without limitation, by calculating a peak R-wave amplitude and an average signal amplitude over a complete cardiac cycle and comparing the two by division or subtraction; by calculated a peak or average signal magnitude or amplitude for a QRS complex and comparing to a peak or average signal amplitude or magnitude for a period of time associated with a T-wave or the T-wave itself.

If a noise detection analysis is performed on detected cardiac cycles, or on the signal generally, whichever of 206 or 212 has fewer noise markers. For an example of noise analysis, see U.S. Pat. No. 7,248,921, the disclosure of which is incorporated herein by reference. In one example, a quantity of turning points or inflection points in the sensed cardiac signal associated with a cardiac cycle detection is compared to a threshold and, if the threshold is exceeded, a noise detection is declared.

If overdetection analysis is performed on detected cardiac cycles, whichever of 206 or 212 has fewer overdetection markers. For examples of overdetection analysis, see U.S. Pat. Nos. 8,160,686 and 8,160,687, the disclosures of which are incorporated herein by reference. In one example, correlation analysis is used and if a sequence of three correlations are performed against a template with result of high correlation for two detected cardiac cycles around low correlation for a third cardiac cycle detection, the third cardiac cycle detection is found to be overdetected. In another example, if the intervals between detected cardiac cycle match a pattern for overdetection of, for example, long-short-long (or more complex patterns may be used), one or more detected cardiac cycles are declared to be overdetected. In still another example, if two cardiac cycle detections occur very close together in time with specific morphology or polarity, double detection of a QRS complex may be declared. In yet another example, a detected cardiac cycle is compared to at least two preceding detected cardiac cycles and, if the immediately preceding cycle detection does not match the detected cardiac cycle, but the cycle detection two prior does match the detected cardiac cycle, the immediately preceding cardiac cycle detection is declared to be overdetected.

If R-wave and T-wave amplitudes can be estimated for cardiac cycles, the ratio of R:T may be calculated, with a higher ratio indicating likely better sensing. U.S. Pat. No. 7,623,909 shows some examples of finding R:T ratios. For example, following a cardiac cycle detection, a peak occurring during a first time period (for example, the 200 to 300 milliseconds preceding and following the cardiac cycle detection) may be presumed to be the R-wave and a peak occurring during a second time period, such as a time period starting 200 to 300 milliseconds after the cardiac cycle detection and lasting about 300 milliseconds, may be deemed to be the T-wave, assuming also that the actual cardiac rate is less than 120 beats per minute or so.

If a morphology analysis block is available, signal attributes may include calculation of the similarity of each detected cardiac cycle to adjacent cycles and/or to a stored template. If one or the other of blocks 206 and 212 shows a stronger correlation over time, this may indicate which signal is better functioning. U.S. Pat. Nos. 8,160,686 and 8,160,687 each discuss different variants on comparison of detected cardiac cycles to one or more static or dynamic template.

Again using a morphology analysis block, whether a high scoring template comparison can be had using multiple cardiac cycle signals may serve as another signal quality indicator using, for example, the methods of U.S. Pat. Nos. 7,477,935 and 7,376,458, the disclosures of which are incorporated herein by reference.

Other comparisons may be made as well at 220, and the invention should not be understood as being limited to any of the above.

The above methods in FIGS. 4-6 may be performed while a patient is in-clinic or ambulatory. Because signal quality data is being gathered, it may be suitable to limit some methods to in-clinic use under supervision of a physician, so that patient activity or external events (such as working next to high power equipment) does not create untoward outcomes. In some examples, a patient activity monitor may be used, such as an accelerometer, and the methods may be limited to performance while the patient is found to be at rest or sleeping.

Figure 7:
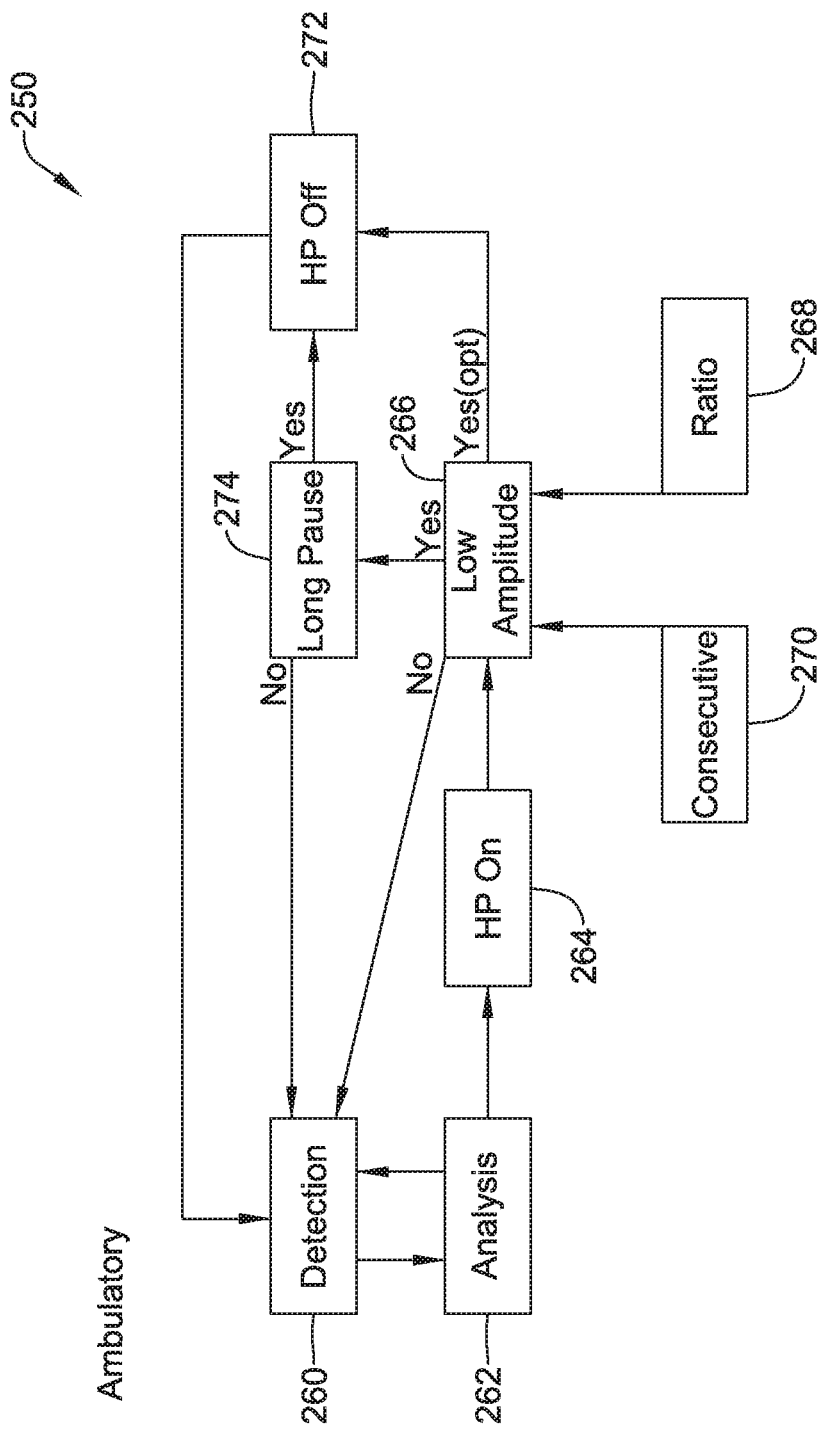

FIG. 7 shows another illustrative method in block flow form. This example is designed for operation while the patient is ambulatory, as indicated at 250, and operates with the HP filter on, as noted at 264. The activity here includes ordinary cardiac cycle detection at 260 and analysis at 262, which may take any of numerous forms known in the art and implemented in various commercially available cardiac rhythm management devices such as implantable cardioverter defibrillators, the S-ICD System, cardiac resynchronization devices, pacemakers, wearable defibrillators, and other products.

The method diverges from these prior implementations by noting that the HP filter is on at 264 and performing analysis to ensure that the patient's sensed signals are not becoming inadequate. A first tier check is noted at 266, where a count of low amplitude signals is made. The count of low amplitude signals 266 may call for a set of consecutive detected cardiac cycles to have low amplitude, or a set of sensed data to remain below a threshold, yielding consecutive data 270. Alternative, the count of low amplitude signals 266 may look at a ratio of low amplitude events within a set of events or time; for example, if 10 of 18, or some other ratio, of consecutive detected events have an amplitude below a threshold.

If low amplitude is found at 266, in one example, the HP filter is simply turned off, at 272, in the hopes that this will improve amplitudes and move away from the noise floor. In another example, a time-based, second check is also performed, as noted at 274. In this example, if block 266 is satisfied, then a long pause, or several long pauses, may be sought out, as indicated at 274. This additional step at 274 may be provided to ensure that the low amplitude signal is actually affecting sensing by causing what may appear to be undersensing. If the long pause(s) requirement at 274 is met, then the HP filter is turned off at 272. If either of blocks 266 or 274 fail, the method returns to the ordinary detection/analysis cycle 260/262.

In one example, block 266 calls for a consecutive set of 1 to 100 beats with amplitude below a threshold in the range of three to six times the noise floor of a system. In the embodiment tested, the noise floor was at 80 microvolts and the low amplitude thresholds tested were 250 and 500 microvolts, with sets of 1, 5 and 100 beats tested. Lower numbers and higher thresholds will turn the HP filter off more readily. In this example, block 274 was omitted/bypassed.

In another example, block 266 calls for an X out of Y approach, or ratio 268. Tested quantities were 10/24 and 18/24, with the amplitude boundaries again at three to six times the noise floor of the tested system. The lower quantity for X would again be more aggressive, however it would take a longer period of time to fill the buffer with such a number of events than some of the shorter contiguous event tests (1 and 5) noted just above. In this example, block 274 was omitted/bypassed.

In another example, a test called for five consecutive events having an amplitude below three times the noise floor (250 microvolts in a system with an 80 microvolt noise floor, in this example), for block 266, and also called for at least two out of five previously detected cardiac cycles to be separated by intervals of more than 1200 milliseconds. In further testing, the interval was extended to 1400 milliseconds. In some embodiments, a timeout may take place without a detected cardiac event; in one example, a two-second timeout takes place if there is no detected cardiac cycle, resetting a detection timer to zero. In this example, if the signals sensed during the two second period leading to the timeout fail to exceed the amplitude threshold, the two second period may be counted as one of the contiguous low amplitude detected cardiac cycles.

Specific references to a particular implementation should be understood as illustrative; it is sufficient that a process is disclosed in FIG. 7 whereby low amplitude or low amplitude in combination with long pause(s) may be assessed to determine that the HP filter can be disabled at block 272.

Figure 8:
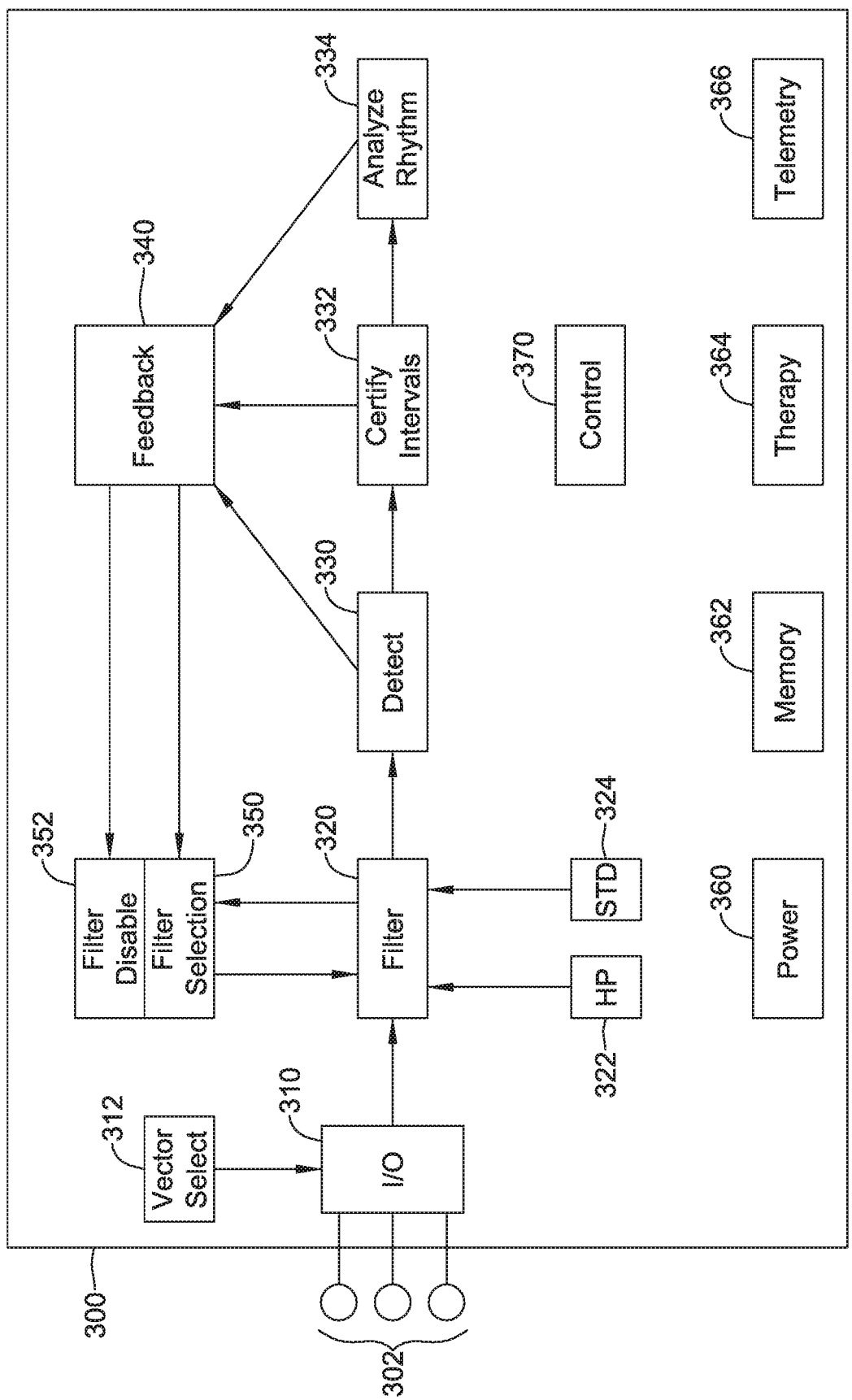
FIG. 8 provides another depiction of an illustrative cardiac rhythm management with functional blocks and data flow connections shown.

FIG. 8 provides another depiction of an illustrative cardiac rhythm management with functional blocks and data flow connections shown. The illustrative device 300 includes a plurality of electrodes 302 coupled to input/output (I/O) circuitry at 310, which may include switches or a multiplexor that facilitate vector selection 312 to choose a preferred sensing vector from among the available electrode pairs. From the I/O circuit 310, the signal proceeds to a filter block 320. Filtering may include or exclude a high pass (HP) filter 322 in addition to standard filtering 324. The filtered signal from block 320 goes to a detection block 330, where individual cardiac cycles are detected by, for example, comparing a sensed signal to a time-varying amplitude threshold. Intervals between the detected cardiac cycles are then analyzed for certification at 332 by, for example, eliminating noise and/or overdetection. The overall cardiac rhythm can then be analyzed at 334 using the certified intervals from block 332.

Each of blocks 330, 332 and 334 may generate data for use in a feedback loop at 340 that can operate a filter selector at 350 and/or a filter disabling functional block at 352. For example, filter selection 350 may operate using the methods shown above in FIGS. 4-6. Filter disable 352 may operate as shown in FIG. 7. The filter selection block 350 and filter disable block 352 determine whether the filter 320 uses standard filtering 324 alone or in conjunction with the addition a high pass filter 322. The output signal from the filter block 320 may also be used by one or both of blocks 350/352 to analyze the signal as filtered.

The device may also include a number of other functional blocks, such as a power block 360, which may include a rechargeable or primary cell battery, or a super capacitor, or a circuit for receiving power from a remote source such as a coil for receiving power via inductive linkage. A memory 362 is shown and may include suitable random access or read only memory, and/or solid state or flash memory, or other memory circuits and chips. A therapy circuit 364 may be provided and may include, for example, an output capacitor and charger for delivering high voltage output (defibrillation, for example), or lower power circuitry for providing output pacing therapy, or a driver for an actuator to deliver a therapeutic substance, for example. The therapy circuitry 364 may be coupled to the I/O 310. Telemetry circuity 366 may be provided to, for example, facilitate wireless RF or inductive telemetry, or conducted communication, with other devices. Cellular or other communication capabilities may be supported in block 366.

A centralized control module 370 may also be provided, for example, a microcontroller or microprocessor may be included. Several of the functional blocks shown may be provided as dedicated circuits, while others may be performed in a microcontroller using stored instruction sets. The description of FIG. 3, above, provides one example for an architecture.

In an example, vector selection block 312 may represent a module within the controller 370 for providing outputs to configure the I/O circuitry 310, which would be provided as a dedicated or separate circuity. The filter block 320 may include analog and/or digital elements as dedicated ASIC and discrete components, and may integrate therein amplification and analog-to-digital conversion, all of which may operate together and interact in various ways. The filter selector and filter disable blocks at 350, 352 may again be modules within the control block 370 and operate as modules of instruction sets for controlling the operation of the filter block 320.

The detection block 330 may be a dedicated ASIC or set of functional discrete components or circuits within an ASIC, while certification may include multiple elements that appear in discrete components and circuits within an ASIC while also representing modules of implementable instruction sets operated by the control circuit 370. Analysis of the rhythm 334 likely occurs primarily within the control block 334, as would the analysis in the feedback block 340. The instruction sets for operation by the control circuit may be stored in memory in a non-transitory form, such as in a flash memory location or in other controller readable memory.

Some implementations include operational circuitry for receiving a signal from implantable electrodes, processing the signal and analyzing the processed signal to make decisions such as whether to store data or deliver therapy. Operational circuitry may be housed in a canister or canisters. The operational circuitry may include a controller (such as a microcontroller or microprocessor, or simply an application specific integrated chip (ASIC) such as an analog, mixed signal, or digital ASIC). The operational circuitry may include suitable analog and/or digital circuits needed for signal processing, memory storage and generation of high-power electrical, low-power electrical and/or non-electrical outputs. The operational circuitry may include suitable battery technology for an implantable device (rechargeable or primary cell), with any of numerous examples well known in the art, and may use various capacitor technologies to assist in the short term build-up and/or storage of energy for defibrillation or other output purposes.

Implantable or wearable components may be manufactured with biocompatible materials suitable for implantation or tissue contact, such as those widely known, along with coatings for such materials, throughout the art. For example, implantable devices can be made using titanium, with a titanium nitride or iridium oxide (or other material) coating if desired, and implantable leads can be formed with a biocompatible material such as a polyether, polyester, polyamide, polyurethane, polycarbonate, silicon rubber and blends or copolymers thereof. Alternatively, other biocompatible materials such as silver, gold, titanium, or stainless steel such as MP35N stainless steel alloy, or other materials may be used.

In some examples, the system may include one or more sensors to detect signals in addition to the cardiac electrical signal that can be captured using selected combinations of implantable or wearable electrodes. Such additional sensors may include, for example, temperature sensors, accelerometers, microphones, optical sensors and chemical sensors, among others. The programmer 22 and implantable device 12 (FIG. 2) may communicate with one another using, for example and without limitation, inductive or RF telemetry, or any other suitable communication solution, including conducted communication. The present invention may be embodied in a system having any such characteristics.

In the following non-limiting examples, where a flow diagram is referenced relative to a means term or device element, it may be understood that the means or device may be a circuit having logic, analog and or digital functional elements configured to perform an illustrative step or may comprise a stored instruction set for execution by a controller or processor of a given device.

A first non-limiting example takes the form of a cardiac rhythm management device comprising plural sensing electrodes for capturing a cardiac signal and operational circuitry coupled to the plural sensing electrodes for analyzing the cardiac signal. FIG. 2 shows an example of such a system having electrodes available for sensing at each of 12, 16, 18 and 20, and operational circuitry contained in the canister 12 as described above and also shown in FIG. 3 and FIG. 8. In the first non-limiting example, the operational circuitry comprises the following: filter means for filtering the captured cardiac signal according to a first approach and a second approach, the second approach applying an additional high pass filter relative to the first approach (see FIG. 3, with filtering at 66 and 72 where the switch 82 determines whether the additional filter at 72 is included in the signal passed on for morphology and/or detection analysis; also FIG. 8 with filter 320 and selection block 350 controlling whether standard filtering 324 is used alone or with high pass filter 322); selector means coupled to the filter means for determining whether to select the first approach or the second approach for the filter means (switch 82, for example, as shown in FIG. 3, and/or selection block 350 in FIG. 8), wherein the selector means is configured to determine a first amplitude of the captured cardiac signal, post filtering via the first approach, and compare the first amplitude to a first threshold (such configuration of the selector means is illustrated in the flow diagram of FIG. 4 and may be implemented in hardware or as instructions for operation by a controller or processor for example and or applied in FIG. 8 via controller 370 or filter block 320 with filter selection block 350) and: if the first amplitude exceeds the first threshold, enable the second approach for use in cardiac signal analysis (In FIG. 4, Yes at block 104 passing to block 108, implemented for example in the systems shown in FIG. 3 or FIG. 8); or if the first amplitude does not exceed the first threshold, disable the second approach for use in cardiac signal analysis (In FIG. 4, No at block 104 leading to block 106 where the HP filter is turned off, implemented for example in the systems shown in FIG. 3 or FIG. 8); and cardiac cycle detector means for comparing a received cardiac signal, as filtered by one of the first or second approaches, to a detection threshold and declaring a new cardiac cycle when the received cardiac signal exceeds the detection threshold (detection means are illustratively shown at FIG. 3, block 76 and again in FIG. 8, block 330).

A second non-limiting example take the form of a cardiac rhythm management device as in the first non-limiting example wherein the selector means is further configured, subsequent to enabling the second approach for use in cardiac signal analysis, to determine a second amplitude of the captured cardiac signal after filtering via the second approach, and compare the second amplitude to a second threshold, the second threshold being lower than the first threshold, and, if the second amplitude does not exceed the second threshold, to disable the second approach for use in cardiac signal analysis. Such means are shown, for example, in FIG. 4, block 110 and 112 or 106, implemented for example in the systems shown in FIG. 3 or FIG. 8 such as by using the feedback block 340 as a separate circuit block or ASIC and/or via instructions operated by the controller or processor 370.

A third non-limiting example takes the form of a cardiac rhythm management device as in the second non-limiting example, further comprising disabling means for disabling the second approach, after it has been selected by the selector means, wherein the disabling means is configured to determine a third amplitude of the captured cardiac signal, as filtered via the second approach, and compare the third amplitude to a third threshold, and, if the third amplitude does not exceed the third threshold, disable the second approach. Disabling means are highlighted at 352 in FIG. 8 taking information from the feedback at 340 which can implement the methods of FIG. 7 where the low amplitude block 266 facilitates a decision to turn off the HP filter at 272.

A fourth non-limiting example takes the form of a cardiac rhythm management device as in the second non-limiting example further comprising disabling means for disabling the second approach, the disabling means comprising: interval means to analyze intervals between cardiac cycles detected by the detection means and determining whether plural such intervals exceed one or more predefined thresholds and, if so, to declare long pauses have occurred; amplitude means for observing whether one or more amplitudes associated with one or more cardiac cycles detected by the detection means fail to meet one or more minimum amplitude thresholds and, if so, to declare low amplitude;

and the disabling means is configured to disable the second approach if both long pauses and low amplitude have been declared at the same time. Example amplitude and interval means are illustrated in FIG. 7 at blocks 266 and/or 274, and disabling means at block 272, with the amplitude and interval assessments forming operational parts of the feedback 340 in FIG. 8 and disabling block at 352 of FIG. 8.

A fifth non-limiting example takes the form of a cardiac rhythm management device as in the second non-limiting example, further comprising disabling means for disabling the second approach, the disabling means comprising interval means to analyze intervals between cardiac cycles detected by the detection means and determining whether plural such intervals exceed one or more predefined thresholds and, if so, to declare long pauses have occurred; and the disabling means is configured to disable the second approach long pauses have been declared. Interval analysis is shown in FIG. 7 at 274 in relation to identifying a long pause (or long pauses), triggering disabling at 272; such may be operational parts of the feedback 340 in FIG. 8 and disabling block at 352 of FIG. 8.

A sixth non-limiting example takes the form of a cardiac rhythm management device as in the second non-limiting example, further comprising disabling means for disabling the second approach, the disabling means comprising amplitude means for observing whether one or more amplitudes associated with one or more cardiac cycles detected by the detection means fail to meet one or more minimum amplitude thresholds and, if so, to declare low amplitude; and wherein the disabling means is configured to disable the second approach if low amplitude has been declared. Amplitude is assessed at 266 in FIG. 7 and linked to disabling at 272; such may be operational parts of the feedback 340 in FIG. 8 and disabling block at 352 of FIG. 8.

A seventh non-limiting example takes the form of a cardiac rhythm management device comprising plural sensing electrodes for capturing a cardiac signal (for example as shown in FIG. 2) and operational circuitry coupled to the plural sensing electrodes for analyzing the cardiac signal (for example as shown in FIGS. 3 and/or 8), the operational circuitry comprising the following: filter means for filtering the captured cardiac signal according to a first approach and a second approach, the second approach applying an additional high pass filter relative to the first approach (for example, FIG. 3 with filters at 66 and the additional highpass at 72; also FIG. 8 at 320 with filter options at 322 and 324); and selector means coupled to the filter means for determining whether to select the first approach or the second approach for the filter means (selections illustrated using a switch at 82 in FIG. 3, or the selection and disable blocks at 350, 352 in FIG. 8), wherein the selector means is configured to operate the device to capture data using each of the first approach and the second approach, to analyze the data captured with each of the first and second approaches, and to determine which of the first approach or second approach yields more suitable sensing data (for example, in FIG. 5, vector selection may be performed to yield results at 156, 164 with the different filters chosen and then compared together at 166; in addition, in FIG. 6, attributes are measured at 206, 212 in and assessed at 220).

An eighth non-limiting example takes the form of a cardiac rhythm management device as in the seventh non-limiting example, further comprising vector selection means for performing a vector selection sequence using signals from at least first and second sensing vectors defined by the plurality of electrodes, wherein the selector means is configured to activate the vector selection means with the first approach enabled to yield a first selected vector, and again with the second approach enabled to yield a second selected vector, and the selector means is configured to determine which of the first approach or second approach yields more suitable sensing data by assessing: a) whether the first selected vector and the second selected vector are the same sensing vector; and b) whether an amplitude measure for the second selected vector exceeds an amplitude threshold; such that, if both a) and b) are true, the selector means is configured to select the second approach, and otherwise the selector means is configured to select the first approach. For example, FIG. 5 shows that vector selection capability is called upon at blocks 154 and 162 to provide outputs or results at 156, 164, respectively for comparison at block 166 and use in enabling or disabling the filtering approach including an extra high pass filter at 170, 172; FIG. 8 illustrates the inclusion of vector selection block 312 used to control the input/output subcircuit 310 which can then drive the feedback loop at 340 in an example, as managed by the controller/processor 370).

A ninth non-limiting example takes the form of a cardiac rhythm management device as in the seventh non-limiting example further comprising cardiac cycle detector means for comparing a received cardiac signal, as filtered by one of the first or second approaches, to a detection threshold and declaring a new cardiac cycle when the received cardiac signal exceeds the detection threshold; wherein the selector means is configured to operate the cardiac cycle detector as follows: in a first data stream, on data filtered using the first approach; and in a second data stream, on data filtered using the second approach; to yield two sets of detected cardiac cycle data, wherein the selector means is configured to align the two sets of data and determine which of the first approach and second approach is providing more accurate cardiac cycle detection. For example, FIG. 6 shows data analysis that may perform the gathering and attribute calculations for a first data stream via the combination of blocks 204, 206, and a second data stream at 210, 212 with the HP filter on, for provision to an assessment block at 220 then driving the determination of which filter approach to select as between blocks 222 and 224; such may be used in FIG. 3 with data provided to the detector block 76 to generate cardiac cycle data, and also in FIG. 8 with the feedback at 340 observing attributes from the detection block 330 which may operate on multiple data streams at once in a parallel processing approach or may alternatively operate in sequential fashion on different sets of data.

A tenth non-limiting example takes the form of a cardiac rhythm management device as in the ninth non-limiting example, further comprising a noise identifier for determining whether one or more detected cardiac cycles are noisy; wherein the selector means is configured to use the noise identifier to select whichever of the first and second approaches yields fewer noisy detected cardiac cycles. Such is illustrated in FIG. 8 where the certification of intervals at 332 can parallel process, or sequentially process, detected cardiac cycles from block 330 using noise analysis, as described above in several examples.

An eleventh non-limiting example takes the form of a cardiac rhythm management device as in the ninth non-limiting example, further comprising an overdetection identifier for determining whether one or more detected cardiac cycles are overdetected; wherein the selector means is configured to use the overdetection identifier to select whichever of the first and second approaches yields fewer overdetected cardiac cycles. Such is illustrated in FIG. 8 where the certification of intervals at 332 can parallel process, or sequentially process, detected cardiac cycles from block 330 using overdetection analysis, as described above in several examples.

A twelfth non-limiting example takes the form of a cardiac rhythm management device as in the ninth non-limiting example, further comprising wave identifier means for identifying R-waves and T-waves associated with individual detected cardiac cycles and calculating an R:T ratio for each of the first and second approaches; wherein the selector means is configured to use the wave identifier to select whichever of the first and second approaches yields a larger R:T ratio. For example, a wave identifier may form part of the detection block 330 and/or certification block 332 shown in FIG. 8 by, for example, differentiating R and T waves from one another using amplitude and/or timing thresholds or by reference to secondary signals which can align the R-wave to cardiac contraction using heart sounds or blood pressure metrics, or pulse oximetry to identify blood flow, from which T-wave repolarization would be separated in time; such can be implemented in the Feedback loop 340 to control filter selection and/or disabling blocks 350, 352.

A thirteenth non-limiting example takes the form of a cardiac rhythm management device as in the seventh non-limiting example, wherein the selector means is configured to determine whether an amplitude measure of the signal as sensed using the first approach exceeds a first threshold and, if not, identify the first approach as yielding more suitable sensing data. For example, an amplitude measure may be one of the attributes generated at blocks 204 and 210 in FIG. 6 and provided via blocks 206, 212 to the assessment block at 220, using for example a method as illustrated in FIG. 4 at blocks 102/104, performed by the feedback loop, for example, at 340 in FIG. 8 to then control the filter selection and disabling blocks 350, 352.

A fourteenth non-limiting example takes the form of a cardiac rhythm management device as in the thirteenth non-limiting example wherein the selector means is configured such that, if the amplitude measure of the signal as sensed using the first approach does exceed the first threshold, the selector means is further configured to determine whether an amplitude measure of the signal as sensed using the second approach exceeds a second threshold and: if the signal as sensed using the second approach exceeds the second threshold, to identify the second approach as yielding more suitable sensing data; and otherwise to identify the first approach as yielding more suitable sensing data. For example, an amplitude measure may be one of the attributes generated at blocks 204 and 210 in FIG. 6 and provided via blocks 206, 212 to the assessment block at 220, using for example a method as illustrated in FIG. 4 at blocks 108/110, performed by the feedback loop, for example, at 340 in FIG. 8 to then control the filter selection and disabling blocks 350, 352.

A fifteenth non-limiting example takes the form of a cardiac rhythm management device as in any of the eighth to fourteenth non-limiting examples further comprising disabling means for controlling the filtering means and disabling the second approach if a combination of sensed amplitudes with the second sensing approach and intervals between cardiac event detections detected on a signal filtered using the second approach suggest possible undersensing. For example, FIG. 7 shows such a method and may be implemented by the feedback loop for example at 340 in FIG. 8.

A sixteenth non-limiting example takes the form of a cardiac rhythm management device as in any of the first fifteen examples, in which the first approach uses a bandpass filtering in the range of 3 to 40 hertz, and the second approach uses the same bandpass as the first approach with an additional highpass filter at about 9 hertz. For example, FIGS. 3 and 8 show systems having an additional highpass filter for swapping into or out of the sensing process for cardiac signals.

A seventeenth non-limiting example takes the form of a cardiac rhythm management device as in any of the first sixteen examples, further comprising therapy circuitry for providing a defibrillation stimulus wherein the device is a subcutaneous-only implantable defibrillator. Therapy circuitry is shown in FIG. 8 at 364, and a subcutaneous-only implantable defibrillator is illustrated in FIG. 2.

An eighteenth non-limiting example takes the form of a cardiac rhythm management device comprising plural sensing electrodes for capturing a cardiac signal and operational circuitry coupled to the plural sensing electrodes for analyzing the cardiac signal, the operational circuitry configured with a selectable filtering mode allowing filtering the captured cardiac signal according to a first approach and a second approach, the second approach applying an additional high pass filter relative to the first approach, wherein the operational circuitry is configured to operate using the selectable filtering mode as follows: determining whether to select the first approach or the second approach by measuring a first amplitude of the captured cardiac signal, post filtering via the first approach, and comparing the first amplitude to a first threshold and: if the first amplitude exceeds the first threshold, enabling the second approach for use in cardiac signal analysis; or if the first amplitude does not exceed the first threshold, disabling the second approach for use in cardiac signal analysis; and detecting cardiac cycles by comparing a received cardiac signal, as filtered by one of the first or second approaches, to a detection threshold and declaring a new cardiac cycle when the received cardiac signal exceeds the detection threshold.

A nineteenth non-limiting example takes the form of a cardiac rhythm management device as in the eighteenth non-limiting example, wherein the operational circuitry is further configured, subsequent to enabling the second approach for use in cardiac signal analysis, to: determine a second amplitude of the captured cardiac signal after filtering via the second approach; compare the second amplitude to a second threshold, the second threshold being lower than the first threshold; and, if the second amplitude does not exceed the second threshold, disable the second approach for use in cardiac signal analysis. A twentieth non-limiting example takes the form of cardiac rhythm management device as in the nineteenth non-limiting example, wherein the operational circuitry is further configured to disable the second approach, after it has been selected for use, in response to determining that a third amplitude of the captured cardiac signal, as filtered via the second approach, fails to exceed a third threshold.

A twenty-first non-limiting example takes the form of a cardiac rhythm management device as in the nineteenth non-limiting example, wherein the operational circuitry is configured to disable the second approach by performing the following: analyzing intervals between detected cardiac cycles and determining whether plural such intervals exceed one or more predefined thresholds and, if so, to declare long pauses have occurred; observing whether one or more amplitudes associated with one or more detected cardiac cycles fail to meet a minimum amplitude threshold and, if so, to declare low amplitude; and the operational circuitry is configured to disable the second approach if both long pauses and low amplitude have been declared at the same time.

A twenty-second non-limiting example takes the form of a cardiac rhythm management device as in the nineteenth non-limiting example, wherein the operational circuitry is configured to disable the second approach by analyzing intervals between detected cardiac cycles and determining whether plural such intervals exceed one or more predefined thresholds and, if so, to declare long pauses have occurred and disable the second approach.

A twenty-third non-limiting example takes the form of a cardiac rhythm management device as in the nineteenth non-limiting example, wherein the operational circuitry is configured to disable the second approach by observing whether one or more amplitudes associated with one or more detected cardiac cycles fail to meet a minimum amplitude threshold and, if so, to declare low amplitude and disable the second approach. A twenty-fourth non-limiting example takes the form of a cardiac rhythm management device as any of the nineteenth to twenty-third non-limiting examples, in which the first approach uses a bandpass filtering in the range of 3 to 40 hertz, and the second approach uses the same bandpass as the first approach with an additional highpass filter at about 9 hertz.

A twenty-fifth non-limiting example takes the form of a cardiac rhythm management device comprising plural sensing electrodes for capturing a cardiac signal and operational circuitry coupled to the plural sensing electrodes for analyzing the cardiac signal, the operational circuitry configured with a first filtering mode and a second filtering mode, the second filtering mode applying an additional high pass filter relative to the first filtering mode, wherein the operational circuitry is configured to select between the first and second filtering modes by: capturing data using each of the first filtering mode and the second filtering mode; analyzing the data captured with each of the first and second filtering modes; and determining which of the first filtering mode or second filtering mode yields more suitable sensing data.

A twenty-sixth non-limiting example takes the form of a cardiac rhythm management device as in the twenty-fifth non-limiting example, wherein the operational circuitry is configured to: perform a vector selection sequence using signals from at least first and second sensing vectors defined by the plurality of electrodes in a first iteration with the first filtering mode applied to yield a first selected vector, and in a second iteration with the second filtering mode applied to yield a second selected vector; determining which of the first filtering mode or second filtering mode yields more suitable sensing data by assessing: a) whether the first selected vector and the second selected vector are the same sensing vector; and b) whether an amplitude measure for the second selected vector exceeds an amplitude threshold; such that, if both a) and b) are true, the operational circuitry is configured to select and use the second filtering mode for sensing cardiac signals, and otherwise the operational circuitry is configured to select and use the first filtering mode for sensing cardiac signals.

A twenty-sixth non-limiting example takes the form of a cardiac rhythm management device as in the twenty-fourth non-limiting example, wherein the operational circuitry is configured to determine which of the first and second filtering modes yields more suitable sensing data by: detecting cardiac cycles by comparing a received cardiac signal to a detection threshold and declaring a new cardiac cycle when the received cardiac signal exceeds the detection threshold in each of: a first data stream, on data filtered using the first filtering mode; and in a second data stream, on data filtered using the second filtering mode; and thereby yielding two sets of detected cardiac cycle data; aligning the two sets of detected cardiac cycle data; and determining which of the first filtering mode and second filtering mode is providing more accurate cardiac cycle detection.

A twenty-seventh non-limiting example takes the form of a cardiac rhythm management device as in the twenty-sixth non-limiting example, wherein the operational circuitry is configured to determine whether one or more detected cardiac cycles are noisy; and wherein the operational circuitry is configured to find that whichever of the first and second filtering mode has fewer noisy detected cardiac cycles yields more suitable sensing data. A twenty-eighth non-limiting example takes the form of a cardiac rhythm management device as in the twenty-sixth non-limiting example, wherein the operational circuitry is configured to determine whether one or more detected cardiac cycles are overdetected; and wherein the operational circuitry is configured to find that whichever of the first and second filtering modes has fewer overdetected cardiac cycles yields more suitable sensing data.

A twenty-ninth non-limiting example takes the form of a cardiac rhythm management device as in the twenty-sixth non-limiting example, wherein the operational circuitry is configured for: identifying R-waves and T-waves associated with individual detected cardiac cycles; calculating an R:T ratio for each of the first and second filtering modes; and finding that whichever of the first and second filtering modes yields a larger R:T ratio. A thirtieth non-limiting example takes the form of a cardiac rhythm management device as in the twenty-fourth non-limiting example, wherein operational circuitry is configured to determine whether an amplitude measure of the signal as sensed using the first filtering mode exceeds a first threshold and, if not, identify the first filtering mode as yielding more suitable sensing data.

A thirty-first non-limiting example takes the form of a cardiac rhythm management device as in the thirtieth non-limiting example wherein the operational circuitry is further configured such that, if the amplitude measure of the signal as sensed using the first filtering mode does exceed the first threshold, the operational circuitry is configured to: determine whether an amplitude measure of the signal as sensed using the second filtering mode exceeds a second threshold and: if the signal as sensed using the second filtering mode exceeds the second threshold, to identify the second filtering mode as yielding more suitable sensing data; and otherwise to identify the first filtering mode as yielding more suitable sensing data. A thirty-second non-limiting example takes the form of a cardiac rhythm management device as in the twenty-fourth non-limiting example wherein the operational circuitry is configured to determine whether possible undersensing is occurring and, if so, to disable the second filtering mode and activate the first filtering mode.

A thirty-third non-limiting example takes the form of a method of operation in a cardiac rhythm management device comprising plural sensing electrodes for capturing a cardiac signal and operational circuitry coupled to the plural sensing electrodes for analyzing the cardiac signal, the operational circuitry configured with a selectable filtering mode allowing filtering the captured cardiac signal according to a first approach and a second approach, the second approach applying an additional high pass filter relative to the first approach, the method comprising: determining whether to select the first approach or the second approach by measuring a first amplitude of the captured cardiac signal, post filtering via the first approach, and comparing the first amplitude to a first threshold and: if the first amplitude exceeds the first threshold, enabling the second approach for use in cardiac signal analysis; or if the first amplitude does not exceed the first threshold, disabling the second approach for use in cardiac signal analysis; and detecting one or more cardiac cycles by comparing a received cardiac signal, as filtered by one of the first or second approaches, to a detection threshold and declaring a new cardiac cycle when the received cardiac signal exceeds the detection threshold.

A thirty-fourth non-limiting example takes the form of a method as in the thirty-third non-limiting example, further comprising, subsequent to enabling the second approach for use in cardiac signal analysis and detecting one or more cardiac cycles therewith: determining a second amplitude of the captured cardiac signal after filtering via the second approach; comparing the second amplitude to a second threshold, the second threshold being lower than the first threshold; and, if the second amplitude does not exceed the second threshold, disabling the second approach for use in cardiac signal analysis. A thirty-fifth non-limiting example takes the form of a method as in the thirty-fourth non-limiting example further comprising disabling the second approach, after it has been selected for use, in response to determining that a third amplitude of the captured cardiac signal, as filtered via the second approach, fails to exceed a third threshold.

A thirty-sixth non-limiting example takes the form of a method as in the thirty-third non-limiting example, further comprising, subsequent to enabling the second approach for use in cardiac signal analysis and detecting two or more cardiac cycles having intervals therebetween: analyzing intervals between detected cardiac cycles and determining whether plural such intervals exceed one or more predefined thresholds; observing whether one or more amplitudes associated with one or more detected cardiac cycles fail to meet a minimum amplitude threshold; and if plural intervals exceed the one or more predefined thresholds, and one or more detected cardiac cycles fail to meet the minimum amplitude threshold while using the second approach, disabling the second approach. A thirty-seventh non-limiting example takes the form of a method as in the thirty-third non-limiting example, further comprising, subsequent to enabling the second approach for use in cardiac signal analysis and detecting two or more cardiac cycles having intervals therebetween: analyzing intervals between detected cardiac cycles; and determining whether plural such intervals exceed one or more predefined thresholds and, if so, disabling the second approach. A thirty-eighth non-limiting example takes the form of a method as in the thirty-third non-limiting example, further comprising, subsequent to enabling the second approach for use in cardiac signal analysis and detecting two or more cardiac cycles having intervals therebetween, observing whether one or more amplitudes associated with one or more detected cardiac cycles fail to meet a minimum amplitude threshold and, if so, disabling the second approach. A thirty-ninth non-limiting example takes the form of a method as in any of the thirty-third to thirty-eighth non-limiting examples, wherein: the first approach uses a bandpass filtering in the range of 3 to 40 hertz; and the second approach uses a bandpass filtering in the range of about 9 to 40 hertz.

A fortieth non-limiting example takes the form of a method of operation in a cardiac rhythm management device comprising plural sensing electrodes for capturing a cardiac signal and operational circuitry coupled to the plural sensing electrodes for analyzing the cardiac signal, the operational circuitry configured with a selectable filtering mode allowing filtering the captured cardiac signal according to a first approach and a second approach, the second approach applying an additional high pass filter relative to the first approach, the method comprising: filtering cardiac signals with the second approach and analyzing the cardiac signals that have been filtered with the second approach to detect cardiac cycles; determining that conditions indicate a termination of the second approach is appropriate; and switching to use of the first approach for filtering the cardiac signals. A forty-first non-limiting example takes the form of a method as in the fortieth non-limiting example, wherein the step of determining that conditions indicate a termination of the second approach is appropriate comprises: analyzing intervals between detected cardiac cycles and determining whether plural such intervals exceed one or more predefined thresholds; observing whether one or more amplitudes associated with one or more detected cardiac cycles fail to meet a minimum amplitude threshold; and if plural intervals exceed the one or more predefined thresholds, and one or more detected cardiac cycles fail to meet the minimum amplitude threshold while using the second approach, determining that conditions indicate a termination of the second approach is appropriate. A forty-second non-limiting example takes the form of a method as in the fortieth non-limiting example, wherein the step of determining that conditions indicate a termination of the second approach is appropriate comprises: analyzing intervals between detected cardiac cycles; and determining whether plural such intervals exceed one or more predefined thresholds and, if so, determining that conditions indicate a termination of the second approach is appropriate. A forty-third non-limiting example takes the form of a method as in the fortieth non-limiting example, wherein the step of determining that conditions indicate a termination of the second approach is appropriate comprises observing whether one or more amplitudes associated with one or more detected cardiac cycles fail to meet a minimum amplitude threshold.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A cardiac rhythm management device comprising plural sensing electrodes for capturing a cardiac signal and operational circuitry coupled to the plural sensing electrodes for analyzing the cardiac signal, the operational circuitry configured with a selectable filtering mode allowing filtering of the captured cardiac signal according to a first approach and a second approach, the second approach applying an additional high pass filter relative to the first approach, wherein the operational circuitry is configured to operate using the selectable filtering mode as follows:
   determining whether to select the first approach or the second approach by measuring a first amplitude of the captured cardiac signal, post filtering via the first approach, and comparing the first amplitude to a first threshold and:
      if the first amplitude exceeds the first threshold, enabling the second approach for use in cardiac signal analysis; or
      if the first amplitude does not exceed the first threshold, disabling the second approach for use in cardiac signal analysis; and
   detecting cardiac cycles by comparing a received cardiac signal, as filtered by one of the first or second approaches, to a detection threshold and declaring a new cardiac cycle when the received cardiac signal exceeds the detection threshold;
   wherein the first amplitude is an average signal strength of the captured signal.

2. A cardiac rhythm management device as in claim 1 wherein the operational circuitry is further configured, subsequent to enabling the second approach for use in cardiac signal analysis, to:
   determine a second amplitude of the captured cardiac signal after filtering via the second approach;
   compare the second amplitude to a second threshold, the second threshold being lower than the first threshold; and, if the second amplitude does not exceed the second threshold,
   disable the second approach for use in cardiac signal analysis.

3. A cardiac rhythm management device as in claim 1, wherein the operational circuitry is configured to disable the second approach by performing the following:
   analyzing intervals between detected cardiac cycles and determining whether plural such intervals exceed one or more predefined thresholds and, if so, to declare long pauses have occurred;
   observing whether one or more amplitudes associated with one or more detected cardiac cycles fail to meet a minimum amplitude threshold and, if so, to declare low amplitude; and
   the operational circuitry is configured to disable the second approach if both long pauses and low amplitude have been declared at the same time.

4. A cardiac rhythm management device as in claim 1, wherein the operational circuitry is configured to disable the second approach by analyzing intervals between detected cardiac cycles and determining whether plural such intervals exceed one or more predefined thresholds and, if so, to declare long pauses have occurred and disable the second approach.

5. A cardiac rhythm management device as in claim 1, wherein the operational circuitry is configured to disable the second approach by observing whether one or more amplitudes associated with one or more detected cardiac cycles fail to meet a minimum amplitude threshold and, if so, to declare low amplitude and disable the second approach.

6. A cardiac rhythm management device as in claim 1 in which the first approach uses a bandpass filtering in the range of 3 to 40 hertz, and the second approach uses the same bandpass as the first approach with an additional highpass filter at about 9 hertz.

7. A method of operation in a cardiac rhythm management device, the device including plural sensing electrodes for capturing a cardiac signal and operational circuitry coupled to the plural sensing electrodes for analyzing the cardiac signal, the operational circuitry configured with a first filtering mode and a second filtering mode, the second filtering mode applying an additional high pass filter relative to the first filtering mode, wherein the method comprises:
   capturing data using each of the first filtering mode and the second filtering mode;
   analyzing the data captured with each of the first and second filtering modes;
   determining which of the first filtering mode or second filtering mode yields more suitable sensing data by comparing at least one result of the analysis of the data using the first filtering mode to a least one result of the analysis of the data using the second filtering mode;
   applying whichever of the first or second filtering mode yields more suitable sensing data to the cardiac signal; and detecting one or more cardiac cycles in the cardiac signal as filtered using the applied filtering mode.

8. The method of claim 7 further comprising:
performing a vector selection sequence using signals from at least first and second sensing vectors defined by the plurality of electrodes in a first iteration with the first filtering mode applied to yield a first selected vector, and in a second iteration with the second filtering mode applied to yield a second selected vector; and
determining which of the first filtering mode or second filtering mode yields more suitable sensing data by assessing:
a) whether the first selected vector and the second selected vector are the same sensing vector; and
b) whether an amplitude measure for the second selected vector exceeds an amplitude threshold;
such that, if both a) and b) are true, the operational circuitry is configured to select and use the second filtering mode for sensing cardiac signals, and otherwise the operational circuitry is configured to select and use the first filtering mode for sensing cardiac signals.

9. The method of claim 7 wherein the step of determining which of the first and second filtering modes yields more suitable sensing data is performed by:
detecting cardiac cycles by comparing a received cardiac signal to a detection threshold and declaring a new cardiac cycle when the received cardiac signal exceeds the detection threshold in each of:
a first data stream, on data filtered using the first filtering mode; and
in a second data stream, on data filtered using the second filtering mode;
and thereby yielding two sets of detected cardiac cycle data;
aligning the two sets of detected cardiac cycle data; and
determining which of the first filtering mode and second filtering mode provides more accurate cardiac cycle detection.

10. The method of claim 7 wherein the step of determining which of the first and second filtering modes yields more suitable sensing data is performed by:
detecting cardiac cycles by comparing a received cardiac signal to a detection threshold and declaring a new cardiac cycle when the received cardiac signal exceeds the detection threshold in each of:
a first data stream, on data filtered using the first filtering mode; and
a second data stream, on data filtered using the second filtering mode;
thereby yielding two sets of detected cardiac cycle data;
determining whether one or more detected cardiac cycles in at least one of the two sets of detected cardiac cycle data is noisy; and
concluding that whichever of the first and second filtering mode has fewer noisy detected cardiac cycles yields more suitable sensing data.

11. The method of claim 7 wherein the step of determining which of the first and second filtering modes yields more suitable sensing data is performed by:
detecting cardiac cycles by comparing a received cardiac signal to a detection threshold and declaring a new cardiac cycle when the received cardiac signal exceeds the detection threshold in each of:
a first data stream, on data filtered using the first filtering mode; and
a second data stream, on data filtered using the second filtering mode;
thereby yielding two sets of detected cardiac cycle data;
determining whether one or more detected cardiac cycles in at least one of the two sets of detected cardiac cycle data is overdetected; and
concluding that whichever of the first and second filtering modes has fewer overdetected cardiac cycles yields more suitable sensing data.

12. The method of claim 7 wherein the step of determining which of the first and second filtering modes yields more suitable sensing data is performed by:
detecting cardiac cycles by comparing a received cardiac signal to a detection threshold and declaring a new cardiac cycle when the received cardiac signal exceeds the detection threshold in each of:
a first data stream, on data filtered using the first filtering mode; and
a second data stream, on data filtered using the second filtering mode;
thereby yielding two sets of detected cardiac cycle data;
identifying R-waves and T-waves associated with individual detected cardiac cycles in at least one of the first and second data streams;
calculating an R:T ratio for each of the first and second filtering modes; and
finding that whichever of the first and second filtering modes yields a larger R:T ratio yields more suitable sensing data.

13. The method of claim 7 further comprising using the detected cardiac cycles to calculate a cardiac cycle rate, comparing the cardiac cycle rate to a threshold as part of a method of determining whether a malignant arrhythmia is present and, in response to determining that a malignant arrhythmia is present, delivering electrical therapy to the heart of the patient.

14. A method of operation in a cardiac rhythm management device comprising plural sensing electrodes for capturing a cardiac signal and operational circuitry coupled to the plural sensing electrodes for analyzing the cardiac signal, the operational circuitry configured with a selectable filtering mode allowing filtering of the captured cardiac signal according to a first approach and a second approach, the second approach applying an additional high pass filter relative to the first approach, the method comprising:
detecting a plurality of cardiac cycles using the second filtering approach;
analyzing an R-wave amplitude of at least one of the cardiac cycles by comparing to a first amplitude threshold and finding that the R-wave amplitude does not exceed the first amplitude threshold;
in response to finding that the R-wave amplitude does not exceed the first amplitude threshold, disabling the second filtering approach and implementing the first filtering approach; and
detecting at least one cardiac cycle using the first filtering approach by comparing a received cardiac signal, as filtered by the first filtering approach, to a detection threshold and declaring a new cardiac cycle when the received cardiac signal exceeds the detection threshold.

15. A method as in claim 14 further comprising, subsequent to implementing the first filtering approach and disabling the second filtering approach:
analyzing an R-wave amplitude of at least one cardiac cycle detected while using the first filtering approach by comparing to a second amplitude threshold;

determining that the second amplitude threshold is exceeded and, in response thereto, re-enabling the second filtering approach and disabling the first filtering approach.

16. A method as in claim 14 further comprising, subsequent to implementing the first filtering approach and disabling the second filtering approach:
    analyzing one or more detected cardiac cycles for noise, wherein the detected cardiac cycles were detected using the cardiac signal as filtered by the first filtering approach;
    finding noise in at least one of the detected cardiac cycles; and, in response thereto, re-enabling the second filtering approach and disabling the first filtering approach.

17. A method as in claim 14 further comprising, subsequent to implementing the first filtering approach and disabling the second filtering approach:
    analyzing one or more detected cardiac cycles for noise, wherein the detected cardiac cycles were detected using the cardiac signal as filtered by the first filtering approach;
    finding noise in at least one of the detected cardiac cycles; and, in response thereto, analyzing an R-wave amplitude of at least one cardiac cycle detected while using the first filtering approach by comparing to a second amplitude threshold;
    determining that the second amplitude threshold is exceeded and, in response thereto, re-enabling the second filtering approach and disabling the first filtering approach.

18. A method as in claim 14 further comprising, subsequent to implementing the first filtering approach and disabling the second filtering approach:
    analyzing one or more detected cardiac cycles for overdetection, wherein the detected cardiac cycles were detected using the cardiac signal as filtered by the first filtering approach;
    finding overdetection in at least one of the detected cardiac cycles; and, in response thereto, re-enabling the second filtering approach and disabling the first filtering approach.

19. A method as in claim 14 further comprising, subsequent to implementing the first filtering approach and disabling the second filtering approach:
    analyzing one or more detected cardiac cycles for overdetection, wherein the detected cardiac cycles were detected using the cardiac signal as filtered by the first filtering approach;
    finding overdetection in at least one of the detected cardiac cycles; and, in response thereto, analyzing an R-wave amplitude of at least one cardiac cycle detected while using the first filtering approach by comparing to a second amplitude threshold;
    determining that the second amplitude threshold is exceeded and, in response thereto, re-enabling the second filtering approach and disabling the first filtering approach.

20. A method as in claim 14 wherein:
    the first approach uses a bandpass filtering in the range of 3 to 40 hertz; and
    the second approach uses a bandpass filtering in the range of about 9 to 40 hertz.

* * * * *